(12) United States Patent
Spangler-Bickell et al.

(10) Patent No.: US 12,406,409 B2
(45) Date of Patent: Sep. 2, 2025

(54) SYSTEM AND METHOD FOR MOTION COMPENSATION FOR CARDIAC PET IMAGING

(71) Applicant: GE Precision Healthcare LLC, Wauwatosa, WI (US)

(72) Inventors: Matthew Gilbert Spangler-Bickell, Clovis, CA (US); Kuan-Hao Su, Brookfield, WI (US); Floribertus Philippus Martin Heukensfeldt Jansen, Ballston Lake, NY (US); Timothy Wayne Deller, Brookfield, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 568 days.

(21) Appl. No.: 17/878,297

(22) Filed: Aug. 1, 2022

(65) Prior Publication Data

US 2024/0037813 A1  Feb. 1, 2024

(51) Int. Cl.
*G06T 11/00* (2006.01)
*A61B 6/00* (2024.01)
(Continued)

(52) U.S. Cl.
CPC ............ *G06T 11/005* (2013.01); *A61B 6/037* (2013.01); *A61B 6/503* (2013.01); *A61B 6/5217* (2013.01);
(Continued)

(58) Field of Classification Search
CPC ..... G06T 11/005; G06T 3/147; G06T 11/008; G06T 2210/41; A61B 6/037; A61B 6/503;
(Continued)

(56) References Cited

U.S. PATENT DOCUMENTS

| 7,599,540 B2 * | 10/2009 | Koehler | G06T 11/006 |
| | | | 382/128 |
| 10,398,382 B2 * | 9/2019 | Sanders, III | A61B 6/5205 |

(Continued)

FOREIGN PATENT DOCUMENTS

| CN | 103445800 A | * 12/2013 | ............ A61B 5/055 |
| CN | 106251380 A | * 12/2016 | ............ G06T 11/003 |

(Continued)

OTHER PUBLICATIONS

Munoz et al., "MR-Based Cardiac and Respiratory Motion-Compensation Techniques for PET-MR Imaging, " Division of Imaging Sciences and Biomedical Engineering, Department of Biomedical Engineering, Sep. 4, 2015, p. 179-191, CrossMark, King's College London.

(Continued)

*Primary Examiner* — Mahendra R Patel
(74) *Attorney, Agent, or Firm* — Fletcher Yoder, P.C.

(57) ABSTRACT

A computer-implemented method for motion compensation of medical imaging data includes estimating, via a processor, non-periodic motion of a myocardium of a heart due to respiration and/or other body movements throughout a positron emission tomography (PET) scan based on list-mode emission data acquired during the PET scan of the heart of a subject. The method also includes performing, via the processor, event-by-event motion-corrected list-mode reconstruction on the list-mode emission data to generate cardiac images with the non-periodic motion removed.

17 Claims, 8 Drawing Sheets

(51) Int. Cl.
*A61B 6/03* (2006.01)
*A61B 6/50* (2024.01)
*G06T 3/147* (2024.01)

(52) U.S. Cl.
CPC .......... *A61B 6/5264* (2013.01); *A61B 6/5288* (2013.01); *G06T 3/147* (2024.01); *G06T 11/008* (2013.01); *G06T 2210/41* (2013.01)

(58) Field of Classification Search
CPC ... A61B 6/5217; A61B 6/5264; A61B 6/5288; A61B 6/486
USPC ......................................................... 382/131
See application file for complete search history.

(56) References Cited

U.S. PATENT DOCUMENTS

| | | | |
|---|---|---|---|
| 10,863,946 | B2 | 12/2020 | Sanders, III et al. |
| 11,179,128 | B2 * | 11/2021 | Heukensfeldt Jansen .................. A61B 6/037 |
| 11,819,357 | B2 * | 11/2023 | Sun ....................... G06T 7/0002 |
| 11,918,390 | B2 * | 3/2024 | Heukensfeldt Jansen .................. G06T 7/0012 |
| 11,963,813 | B2 * | 4/2024 | Nehmeh ............... G01T 1/2018 |
| 12,042,669 | B2 * | 7/2024 | Hu ....................... A61N 5/1068 |
| 12,131,410 | B2 * | 10/2024 | Andreyev ............. G06T 11/008 |
| 2008/0107229 | A1 | 5/2008 | Thomas .................. A61B 6/037 378/207 |
| 2012/0281897 | A1 * | 11/2012 | Razifar ................ A61B 6/5288 250/336.1 |
| 2014/0334702 | A1 * | 11/2014 | El Fakhri ............... A61B 6/037 382/131 |
| 2017/0039738 | A1 * | 2/2017 | Ziv .......................... G01T 1/249 |
| 2018/0317861 | A1 * | 11/2018 | Sun ....................... A61B 6/541 |
| 2018/0353147 | A1 * | 12/2018 | Wang .................... G06T 11/005 |
| 2019/0133542 | A1 * | 5/2019 | Li .......................... A61B 6/5247 |
| 2020/0187874 | A1 * | 6/2020 | Hayden .................. A61B 6/037 |
| 2021/0181282 | A1 * | 6/2021 | Deller .................... G01T 1/1603 |
| 2021/0239863 | A1 * | 8/2021 | Tavitian ................ G06T 11/008 |
| 2021/0264646 | A1 * | 8/2021 | Feng .................... G06T 11/008 |
| 2021/0304457 | A1 * | 9/2021 | Qi ........................... G06T 7/246 |
| 2021/0405226 | A1 * | 12/2021 | Hu ....................... A61B 6/5211 |
| 2022/0047227 | A1 | 2/2022 | Heukensfeldt Jansen |

FOREIGN PATENT DOCUMENTS

| | | | | |
|---|---|---|---|---|
| CN | | 110428384 A * | 11/2019 | .......... G06T 11/005 |
| JP | | 5088994 B2 * | 12/2012 | ............. A61B 5/062 |
| WO | WO-2007015199 | A2 * | 2/2007 | ............. A61B 6/037 |
| WO | WO-2009060348 | A1 * | 5/2009 | ............. A61B 5/0035 |
| WO | WO-2009147605 | A1 * | 12/2009 | .......... G06T 11/008 |
| WO | WO-2012153262 | A1 * | 11/2012 | .......... G06T 11/005 |
| WO | WO-2018083464 | A1 * | 5/2018 | |
| WO | WO-2021154213 | A1 * | 8/2021 | ............. A61B 6/032 |

OTHER PUBLICATIONS

Ambwani et al., "Joint Cardiac and Respiratory Motion Correction and Super-Resolution Reconstruction in Coronary PET/CT," 2011, p. 1702-1705, Boston University, Massachusetts General Hospital, Boston, MA, USA.

Chan et al., "Non-rigid Event-by-event Continuous Respiratory Motion Compensated List-mode Reconstruction for PET," IEEE, 2017, 12 pgs.

Klein et al., "Four-Dimensional Affine Registration Models for Respiratory-Gated PET," Jun. 2001, p. 756-760, vol. 48, No. 3, IEE Transactions on Nuclear Science.

Lamare et al., "List-mode-based reconstruction for respiratory motion correction in PET using non-rigid body transformations," Physics in Medicine and Biology, Aug. 9, 2007, p. 5187-5204, vol. 52, IOP Publishing Ltd., UK.

Lamare et al., "PET respiratory motion correction: quo vadis?," Institute of Physics and Engineering in Medicine, Physics in Medicine & Biology, Feb. 1, 2022, 28 pgs, IOP Publishing, CrossMark.

Spangler-Bickell et al., "Evaluation of Data-Driven Rigid Motion Correction in Clinical Brain PET Imaging," Journal of Nuclear Medicine, Jan. 27, 2022, 23 pgs.

Spangler-Bickell et al., "Ultra-Fast List-Mode Reconstruction of Short PET Frames and Example Applications," The Journal of Nuclear Medicine, 2021, p. 2087-292, vol. 62 No. 2.

Thiruvenkadam et al., "Robust PET Motion Correction Using Non-local Spatio-temporal Priors," 2015, pp. 643-650, Springer International Publishing, Switzerland.

Livieratos et al., "Rigid-Body Transformation of List-Mode Projection Data For Respiratory Motion Correction in Cardiac PET," IEEE Nuclear Science Symposium Conference Record, Oct. 2003, 6 pgs., IEEE, Portland, OR.

Andre Z Kyme et al: "Motion estimation and correction in SPECT, PET and CT", Physics in Medicine and Biology, Institute of Physics Publishing, Bristol GB, vol. 66, No. 18, Sep. 15, 2021 (Sep. 15, 2021), XP020368998, ISSN: 0031-9155, DOI: 10.1088/1361-6560/AC093B [retrieved on Sep. 15, 2021] abstract Sections 2 to 4.

EP application 23188894.2 filed Aug. 1, 2023—extended Search Report issued Dec. 22, 2023; 9 pages.

Fully Three-Dimensional Image Reconstruction in Radiology and Nuclear Medicine Proceedings, Fully3D, Granlibakken Resort, Lake Tahoe, California, Jun. 16, 2013 (Jun. 16, 2013), XP040726403, p. 122-p. 125.

Lamare F et al: "Evaluation of respiratory and cardiac motion correction schemes in dual gated PET/CT cardiac imaging", Medical Physics, AIP, Melville, NY, US, vol. 41, No. 7, Jun. 12, 2014 (Jun. 12, 2014), XP012186443, ISSN: 0094-2405, DOI: 10.1118/1.4881099 [retrieved on Jan. 1, 1901] abstract Sections 2.C to 2.E.

* cited by examiner

SYSTEM AND METHOD FOR MOTION COMPENSATION FOR CARDIAC PET IMAGING

BACKGROUND

The subject matter disclosed herein relates to non-invasive diagnostic imaging, and more particularly, to positron emission tomography (PET).

Positron emission tomography (PET) generates images that represent a distribution of positron-emitting radiotracer within a body of a patient, which may be used to observe metabolic processes in the body and diagnose disease. During operation of a PET imaging system, the patient is initially injected with the radiotracer, which emits positrons as it decays. Each emitted positron may travel a relatively short distance before encountering an electron, at which point an annihilation occurs. When a positron interacts with an electron by annihilation, the entire mass of the positron-electron pair is converted into two 511 keV gamma photons (also referred to as 511 keV events). The photons are emitted in opposite directions along a line of response (LOR). The annihilation photons are detected by detectors that are placed on both sides of the LOR, in a configuration such as a detector ring, as coincident events. Thus, during data acquisition, the detectors detect the coincident events, which reflect a distribution of the radiotracer in the patient's body. An image thus reconstructed from the acquired image data includes the annihilation photon detection information. Typically, the image is reconstructed upon completion of the data acquisition, and it may be unknown if the acquired data is adequate for producing a high quality image until after the image is reconstructed. For example, cardiac imaging in PET is performed over many minutes and is thus susceptible to various types of motion. For example, motion of the myocardium due to the cardiac cycle, motion due to respiration, and bulk body movements may occur. Such motions may result in blurring of the reconstructed image.

BRIEF DESCRIPTION

Certain examples commensurate in scope with the originally claimed subject matter are summarized below. These examples are not intended to limit the scope of the claimed subject matter, but rather these examples are intended only to provide a brief summary of possible examples. Indeed, the subject matter may encompass a variety of forms that may be similar to or different from the examples set forth below.

In one embodiment, a computer-implemented method for motion compensation of medical imaging data is provided. The method includes estimating, via a processor, non-periodic motion of a myocardium of a heart due to respiration and/or other body movements throughout a positron emission tomography (PET) scan based on list-mode emission data acquired during the PET scan of the heart of a subject. The method also includes performing, via the processor, event-by-event motion-corrected list-mode reconstruction on the list-mode emission data to generate cardiac images with the non-periodic motion removed.

In another embodiment, a system for motion compensation of medical imaging data is provided. The system includes a memory encoding processor-executable routines. The system also includes a processing component configured to access the memory and to execute the processor-executable routines, wherein the routines, when executed by the processing component, cause the processing component to perform actions. The actions include estimating non-periodic motion of a myocardium of a heart due to respiration and/or other body movements throughout a positron emission tomography (PET) scan based on list-mode emission data acquired during the PET scan of the heart of a subject. The actions also include performing event-by-event motion-corrected list-mode reconstruction on the list-mode emission data to generate cardiac images with the non-periodic motion removed.

In a further embodiment, a non-transitory computer-readable medium, the computer-readable medium including processor-executable code that when executed by a processor, causes the processor to perform actions. The actions include estimating non-periodic motion of a myocardium of a heart due to respiration and/or other body movements throughout a positron emission tomography (PET) scan based on list-mode emission data acquired during the PET scan of the heart of a subject. The actions also include performing event-by-event motion-corrected list-mode reconstruction on the list-mode emission data to generate cardiac images with the non-periodic motion removed.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
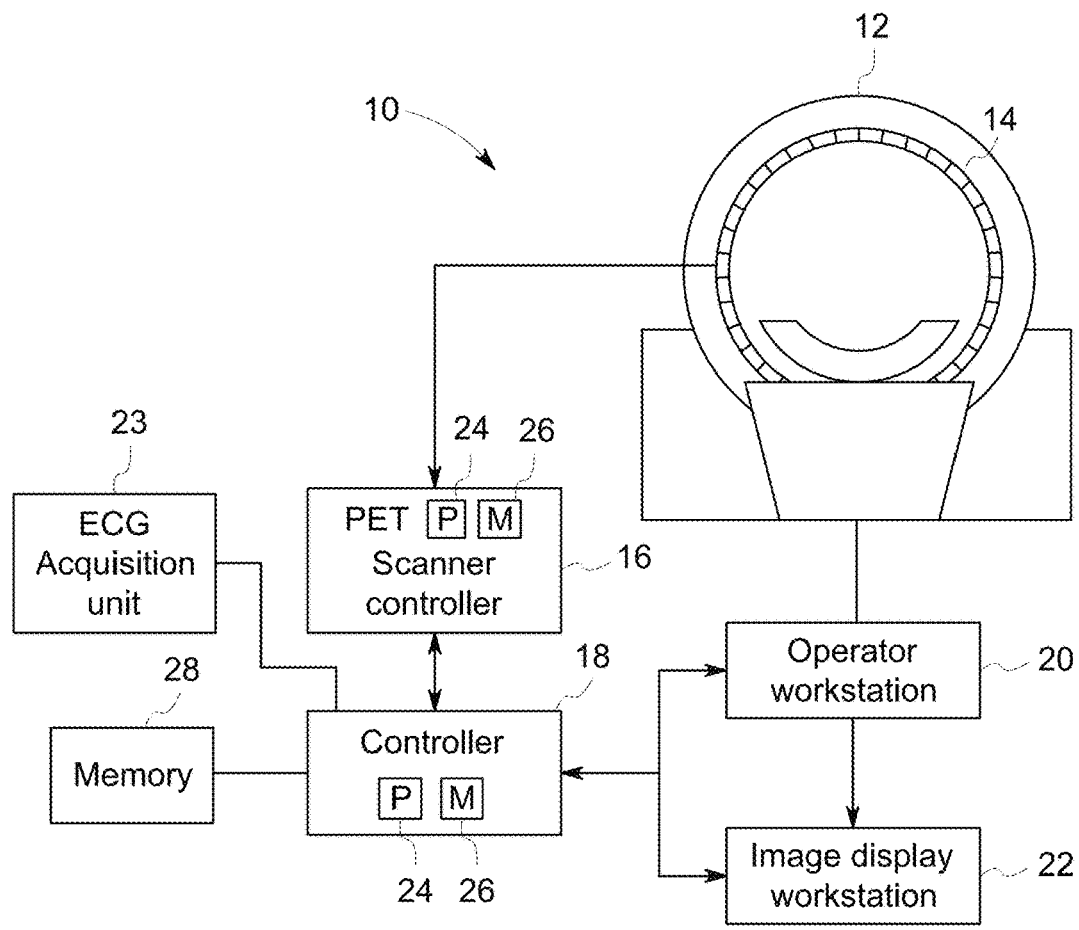
FIG. 1 is a diagrammatical representation of an embodiment of a PET imaging system in accordance with aspects of the present disclosure.

One or more specific examples will be described below. In an effort to provide a concise description of these examples, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various aspects of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed examples.

Cardiac imaging in PET is performed over many minutes and is thus susceptible to various types of motion. For example, motion of the myocardium due to the cardiac cycle, motion due to respiration, and bulk body movements may occur. Such motions may result in blurring of the reconstructed image. The respiratory and bulk body movements can be classified as non-periodic (since irregular breathing is very common). Cardiac motion may be classified as periodic (in almost all cases). All three of these motions result in deformations of the myocardium, but the non-periodic motions deform the myocardium to a far lesser degree than the periodic. Thus, it is reasonable to treat the non-periodic motions as rigid. Rigid motion is much easier to correct for during reconstruction, is much less computationally intensive, and requires fewer approximations and simplifications than incorporating non-rigid motion into the reconstruction.

Present embodiments are generally directed to system and methods for motion compensation of medical imaging data (e.g., PET imaging data). The disclosed embodiments provide for a PET image-based registration technique that enables continuous estimation (e.g., during a PET scan) of respiratory motion with a high temporal resolution (greater than 1 Hertz). In particular, the disclosed embodiments enable correction for the respiratory and bulk movements by adjusting list-mode data on an event-by-event basis, performing a cardiac-gated reconstruction, and non-rigidly aligning the gated images to combine them into a single image. Specifically, the disclosed embodiments include estimating non-periodic motion (e.g., from image space as opposed to gated reconstructions) of a myocardium of a heart (e.g., due to respiratory and bulk body movements) throughout a PET scan based on list-mode emission data acquired during the PET scan of the heart of a subject, performing event-by-event motion-corrected list-mode cardiac-gated reconstruction on the list-mode emission data during the PET scan to generate cardiac-gate images with the non-periodic motion removed, and, subsequent to the PET scan, combining the cardiac-gated images using non-rigid image registration to generate a reconstructed, motion corrected image of the heart (e.g., for a specific gate or an aggregate of all gates). In certain embodiments, the non-periodic motions are assumed to be rigid. The list-mode emission data may be reconstructed (e.g., utilizing ultra-fast list-mode reconstruction) into consecutive frames (e.g., short frames with each frame spanning a second or less or no more than a portion (e.g., 25 percent) of a mean respiratory cycle). In certain embodiments, rigid image registration (e.g., with at least one degree of freedom) may be utilized on the consecutive frames with at least one of the consecutive frames utilized as a reference frame. Estimating non-periodic motion using rigid image registration includes estimating an actual position of the myocardium (e.g., from image space as opposed to gated reconstructions) at every frame of the consecutive frames over an entirety of the PET scan (e.g., without respiratory gating being performed and no periodicity assumed). The disclosed embodiments enable estimating non-period motion using only list-mode data, in a continuous way without assuming periodicity and without external devices (e.g., belt with sensors to detect surface motion due to respiratory movement). The disclosed embodiments enable the generation of motion-corrected cardiac images that are quantitatively more accurate than those without motion correction. In addition, the motion-corrected cardiac images have a superior signal-to-noise ratio compared to respiratory- or cardiac-gated images. These factors result in improved diagnostic quality of the images, more precise measurements of cardiac metrics, and new research opportunities. Further, the disclosed embodiments may lead to reduced scan time for a given signal-to-noise level.

With the foregoing in mind and turning now to the drawings, FIG. 1 depicts a PET or single photon emission computed tomography (SPECT)-computed tomography (CT) system 10 operating in accordance with certain aspects of the present disclosure. The PET or SPECT imaging system of FIG. 1 may be utilized with a dual-modality imaging system such as a PET-CT imaging system described in FIG. 2 or a PET-magnetic resonance imaging (MRI), imaging system described in FIG. 3.

Returning now to FIG. 1, the depicted PET or SPECT system 10 includes a detector 12 (or detector array). The detector 12 of the PET or SPECT system 10 typically includes a number of detector modules or detector assemblies (generally designated by reference numeral 14) arranged in one or more rings, as depicted in FIG. 1, each detector assembly 14 includes multiple detector units (e.g., 3 to 5 detector units or more). The depicted PET or SPECT system 10 also includes a PET scanner controller 16, a controller 18, an operator workstation 20, and an image display workstation 22 (e.g., for displaying an image). In certain embodiments, the PET scanner controller 16, controller 18, operator workstation 20, and image display workstation 22 may be combined into a single unit or device or fewer units or devices. In certain embodiments, an electrocardiogram (ECG) acquisition unit 23 may be coupled to controller 18 to provide ECG signals acquired from a subject (e.g., during a PET scan) for utilization in the techniques described below.

The PET scanner controller 16, which is coupled to the detector 12, may be coupled to the controller 18 to enable the controller 18 to control operation of the PET scanner controller 16. Alternatively, the PET scanner controller 16 may be coupled to the operator workstation 20 which controls the operation of the PET scanner controller 16. In operation, the controller 18 and/or the workstation 20 controls the real-time operation of the PET system or SPECT system 10. In certain embodiments the controller 18 and/or the workstation 20 may control the real-time operation of another imaging modality (e.g., the CT imaging system in FIG. 2) to enable the simultaneous and/or separate acquisition of image data from the different imaging modalities. One or more of the PET scanner controller 16, the controller 18, and/or the operation workstation 20 may include a processor 24 and/or memory 26. In certain embodiments, the PET or SPECT system 10 may include a separate memory 28. The detector 12, PET scanner controller 16, the controller 18, and/or the operation workstation 20 may include detector acquisition circuitry for acquiring image data from the detector 12, image reconstruction and processing circuitry for image processing. The circuitry may include specially programmed hardware, memory, and/or processors.

The processor 24 may include multiple microprocessors, one or more "general-purpose" microprocessors, one or more special-purpose microprocessors, and/or one or more application specific integrated circuits (ASICS), system-on-chip (SoC) device, or some other processor configuration. For example, the processor 24 may include one or more reduced instruction set (RISC) processors or complex instruction set (CISC) processors. The processor 24 may execute instructions to carry out the operation of the PET or SPECT system 10. These instructions may be encoded in programs or code stored in a tangible non-transitory computer-readable medium (e.g., an optical disc, solid state device, chip, firmware, etc.) such as the memory 26, 28. In certain embodiments, the memory 26 may be wholly or partially removable from the controller 16, 18.

In certain embodiments, the processor 24 may execute instructions for motion compensation of PET imaging data. For example, the processor 24 may execute instructions that provide for a PET image-based registration technique that enables continuous estimation (e.g., during a PET scan) of respiratory motion with a high temporal resolution (greater than 1 Hertz). In particular, the processor 24 may execute instructions that enable correction for respiratory and bulk movements by adjusting list-mode data on an event-by-event basis, performing a cardiac-gated reconstruction, and non-rigidly aligning the gated images to combine them into a single image. Specifically, the processor 24 may execute instructions for estimating non-periodic motion (e.g., from image space as opposed to gated reconstructions) of a myocardium of a heart (e.g., due to respiratory and bulk body movements) throughout a PET scan based on list-mode emission data acquired during the PET scan of the heart of a subject, performing event-by-event motion-corrected list-mode cardiac-gated reconstruction on the list-mode emission data during the PET scan to generate cardiac-gated images with the non-periodic motion removed, and, subsequent to the PET scan, combining the cardiac-gated images using non-rigid image registration to generate a reconstructed, motion corrected image of the heart (e.g., for a specific gate or an aggregate of all gates). In certain embodiments, the non-periodic motions are assumed to be rigid. The processor 24 may executed instructions so that the list-mode emission data may be reconstructed (e.g., utilizing ultra-fast list-mode reconstruction) into consecutive frames (e.g., short frames with each frame spanning a second or less or no more than a portion (e.g., 25 percent) of a mean respiratory cycle). In certain embodiments, the processor 24 may execute instructions so that rigid image registration (e.g., with at least one degree of freedom) may be utilized on the consecutive frames with one of the consecutive frames utilized as a reference frame. These instructions include estimating an actual position of the myocardium (e.g., from image space as opposed to gated reconstructions) at every frame of the consecutive frames over an entirety of the PET scan (e.g., without respiratory gating being performed and no periodicity assumed).

By way of example, PET imaging is primarily used to measure metabolic activities that occur in tissues and organs and, in particular, to localize aberrant metabolic activity. In PET imaging, the patient is typically injected with a solution that contains a radioactive tracer. The solution is distributed and absorbed throughout the body in different degrees, depending on the tracer employed and the functioning of the organs and tissues. For instance, tumors typically process more glucose than a healthy tissue of the same type. Therefore, a glucose solution containing a radioactive tracer may be disproportionately metabolized by a tumor, allowing the tumor to be located and visualized by the radioactive emissions. In particular, the radioactive tracer emits positrons that interact with and annihilate complementary electrons to generate pairs of gamma rays. In each annihilation reaction, two gamma rays traveling in opposite directions are emitted. In a PET imaging system 10, the pair of gamma rays are detected by the detector array 12 configured to ascertain that two gamma rays detected sufficiently close in time are generated by the same annihilation reaction. Due to the nature of the annihilation reaction, the detection of such a pair of gamma rays may be used to determine the line of response along which the gamma rays traveled before impacting the detector, allowing localization of the annihilation event to that line. By detecting a number of such gamma ray pairs, and calculating the corresponding lines traveled by these pairs, the concentration of the radioactive tracer in different parts of the body may be estimated and a tumor, thereby, may be detected. Therefore, accurate detection and localization of the gamma rays forms a fundamental and foremost objective of the PET system 10.

Figure 2:
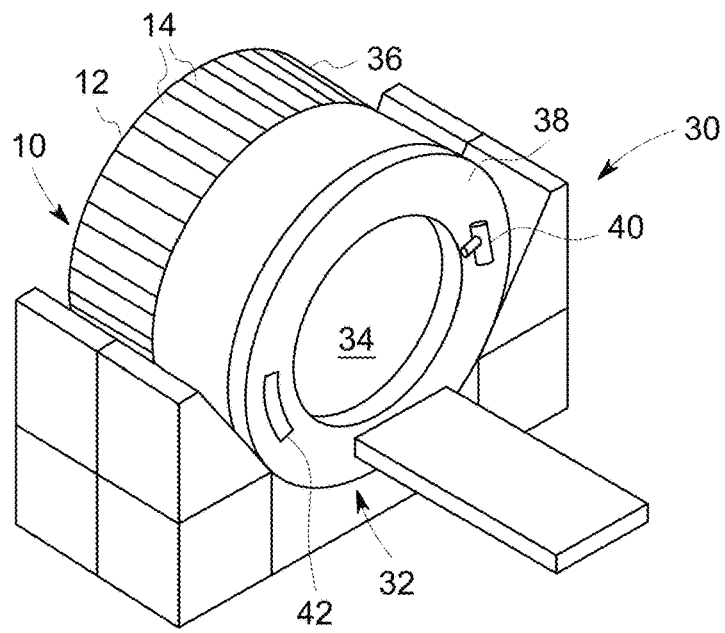
FIG. 2 is a perspective view of a PET-CT imaging system having the PET imaging system of FIG. 1, in accordance with aspects of the present disclosure.

As mentioned above, the PET or SPECT system 10 may be incorporated into a dual-modality imaging system such as the PET-CT imaging system 30 in FIG. 2. Referring now to FIG. 2, the PET-CT imaging system 30 includes the PET system 10 and a CT system 32 positioned in fixed relationship to one another. The PET system 10 and CT system 32 are aligned to allow for translation of a patient (not shown) therethrough. In use, a patient is positioned within a bore 34 of the PET-CT imaging system 30 to image a region of interest of the patient as is known in the art.

The PET system 10 includes a gantry 36 that is configured to support a full ring annular detector array 12 thereon (e.g., including the plurality of detector assemblies 14 in FIG. 1). The detector array 12 is positioned around the central opening/bore 34 and can be controlled to perform a normal "emission scan" in which positron annihilation events are counted. To this end, the detectors 14 forming array 12 generally generate intensity output signals corresponding to each annihilation photon.

The CT system 32 includes a rotatable gantry 38 having an X-ray source 40 thereon that projects a beam of X-rays toward a detector assembly 42 on the opposite side of the gantry 38. The detector assembly 42 senses the projected X-rays that pass through a patient and measures the intensity of an impinging X-ray beam and hence the attenuated beam as it passes through the patient. During a scan to acquire X-ray projection data, gantry 38 and the components mounted thereon rotate about a center of rotation. In certain embodiments, the CT system 32 may be controlled by the controller 18 and/or operator workstation 20 described in FIG. 2. In certain embodiments, the PET system 10 and the CT system 32 may share a single gantry. Image data may be acquired simultaneously and/or separately with the PET system 10 and the CT system 32.

Figure 3:
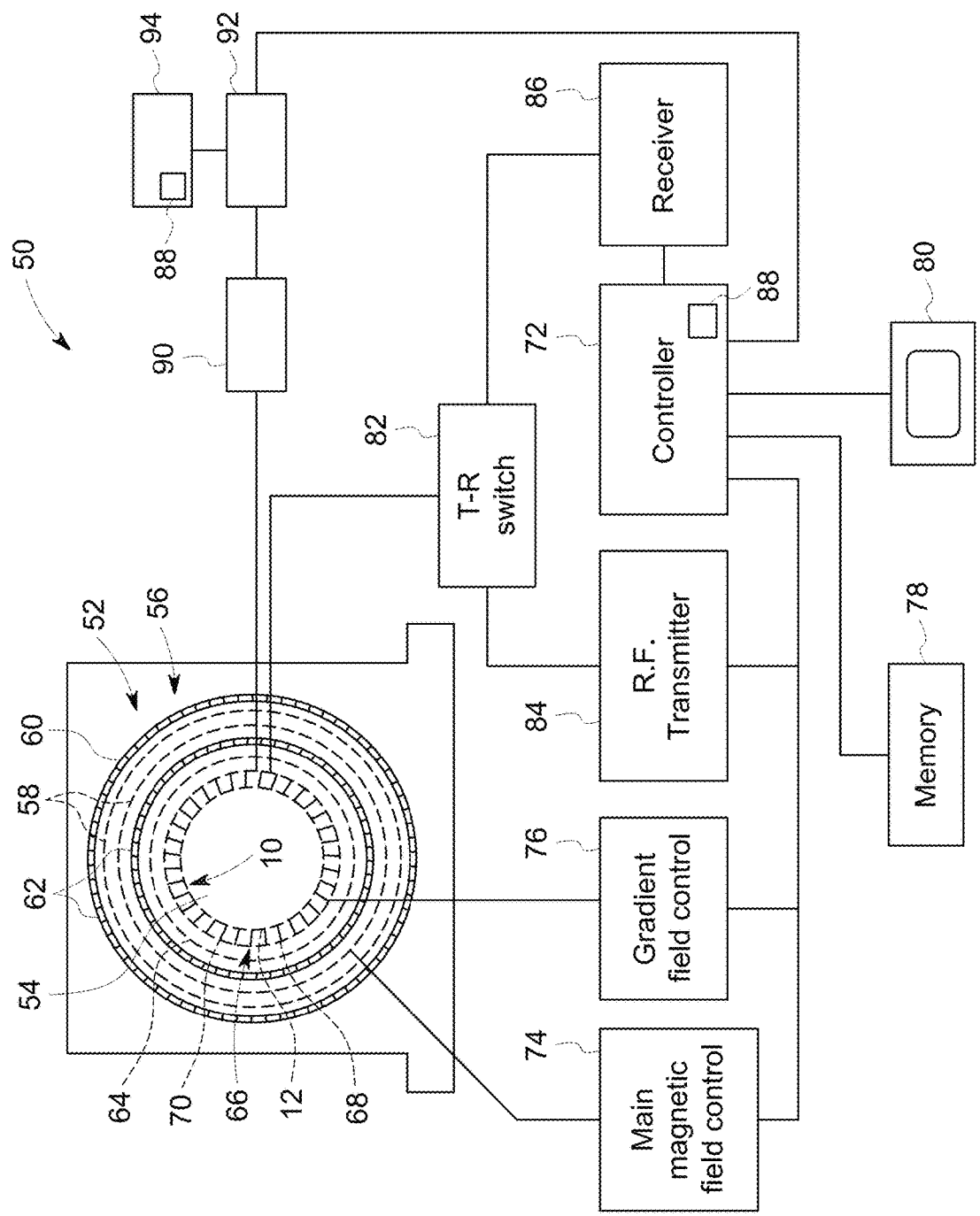
FIG. 3 is a perspective view of a PET-MRI imaging system having the PET imaging system of FIG. 1, in accordance with aspects of the present disclosure.

As mentioned above, the PET or SPECT system 10 may be incorporated into a dual-modality imaging system such as the PET-MM imaging system 50 in FIG. 3. Referring now to FIG. 3, the PET-MRI imaging system 50 includes the PET system 10 and a MM system 52 positioned in fixed relationship to one another. The PET system 10 and MRI system 52 are aligned to allow for translation of a patient (not shown) therethrough. In use, a patient is positioned within a bore 54 of the PET-CT imaging system 50 to image a region of interest of the patient as is known in the art. Image data may be acquired simultaneously and/or separately with the PET system 10 and the MRI system 52.

The PET-MRI imaging system 50 that includes a superconducting magnet assembly 56 that includes a superconducting magnet 58. The superconducting magnet 58 is formed from a plurality of magnetic coils supported on a magnet coil support or coil former. In one embodiment, the superconducting magnet assembly 56 may also include a thermal shield 60. A vessel 62 (also referred to as a cryostat) surrounds the superconducting magnet 58, and the thermal shield 60 surrounds the vessel 62. The vessel 62 is typically filled with liquid helium to cool the coils of the superconducting magnet 58. A thermal insulation (not shown) may be provided surrounding the outer surface of the vessel 62. The imaging system 50 also includes a main gradient coil 64, and an RF coil assembly 66 that is mounted radially inwardly from the main gradient coil 64. As described above, a radio frequency (RF) coil assembly 66 includes the PET detector assembly 12, an RF transmit coil 68 and the RF shield 70. More specifically, the RF coil assembly 66 includes a coil support structure that is used to mount the PET detector assembly 12, the RF transmit coil 68, and the RF shield 70.

In operation, the RF coil assembly 66 enables the imaging system 50 to perform both MM and PET imaging concurrently because both the RF transmit coil 68 and the PET detector assembly 12 are placed around a patient at the center of the bore of the imaging system 50. Moreover, the PET detector assembly 12 is shielded from the RF transmit coil 68 using the RF shield 70 that is disposed between the RF transmit coil 68 and the PET detector assembly 12. Mounting the PET detector assembly 12, the RF coil 68 and the RF shield 70 on the coil support structure enables the RF coil assembly 66 to be fabricated to have an outside diameter that enables the RF coil assembly 66 to be mounted inside the gradient coil 64. Moreover, mounting the PET detector assembly 12, the RF coil 68 and the RF shield 70 on the coil support structure enables the RF coil assembly 66 to have a relatively large inside diameter to enable the imaging system 50 to image larger patients.

The imaging system 50 also generally includes a controller 72, a main magnetic field control 74, a gradient field control 76, a memory 78, a display device 80, a transmit-receive (T-R) switch 82, an RF transmitter 84, and a receiver 86.

In operation, a body of an object, such as a patient (not shown), or a phantom to be imaged, is placed in the bore 54 on a suitable support, for example, a motorized table (not shown) or the cradle described above. The superconducting magnet 58 produces a uniform and static main magnetic field Bo across the bore 54. The strength of the electromagnetic field in the bore 54 and correspondingly in the patient, is controlled by the controller 72 via the main magnetic field control 74, which also controls a supply of energizing current to the superconducting magnet 58.

The main gradient coil 64, which may include one or more gradient coil elements, is provided so that a magnetic gradient can be imposed on the magnetic field Bo in the bore 54 in any one or more of three orthogonal directions x, y, and z. The main gradient coil 64 is energized by the gradient field control 76 and is also controlled by the controller 72.

The RF coil assembly 66 is arranged to transmit magnetic pulses and/or optionally simultaneously detect MR signals from the patient, if receive coil elements are also provided. The RF coil assembly 66 may be selectably interconnected to one of the RF transmitter 84 or receiver 86, respectively, by the T-R switch 82. The RF transmitter 84 and T-R switch 82 are controlled by the controller 72 such that RF field pulses or signals are generated by the RF transmitter 84 and selectively applied to the patient for excitation of magnetic resonance in the patient.

Following application of the RF pulses, the T-R switch 82 is again actuated to decouple the RF coil assembly 66 from the RF transmitter 84. The detected MR signals are in turn communicated to the controller 72. The controller 72 includes a processor 88 that controls the processing of the MR signals to produce signals representative of an image of the patient. The processed signals representative of the image are also transmitted to the display device 80 to provide a visual display of the image. Specifically, the MR signals fill or form a k-space that is Fourier transformed to obtain a viewable image which may be viewed on the display device 80.

The imaging system 50 also controls the operation of PET imaging. Accordingly, in various embodiments, the imaging system 50 may also include a coincidence processor 90 that is coupled between the detector 12 and a PET scanner controller 92. The PET scanner controller 92 may be coupled to the controller 72 to enable the controller 72 to control the operation of the PET scanner controller 92. Optionally, the PET scanner controller 92 may be coupled to a workstation 94 which controls the operation of the PET scanner controller 92. In operation, the exemplary embodiment, the controller 72 and/or the workstation 94 controls real-time operation of the PET imaging portion of the imaging system 50.

More specifically, in operation, the signals output from the PET detector assembly 12 are input to the coincidence processor 90. In various embodiments, the coincidence processor 90 assembles information regarding each valid coincidence event into an event data packet that indicates when the event took place and the position of a detector that detected the event. The valid events may then be conveyed to the controller 92 and utilized to reconstruct an image. Moreover, it should be realized that images acquired from the MR imaging portion may be overlaid onto images acquired from the PET imaging portion. The controller 72 and/or the workstation 94 may a central processing unit (CPU) or computer 88 to operate various portions of the imaging system 50. As used herein, the term "computer" may include any processor-based or microprocessor-based system configured to execute the methods described herein. Accordingly, the controller 72 and/or the workstation 94 may transmit and/or receive information from the PET detector assembly 12 to both control the operation of the PET detector assembly 12 and to receive information from the PET detector assembly 12.

The various embodiments and/or components, for example, the modules, or components and controllers therein, such as of the imaging system 50, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the disclosed subject matter. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 4:
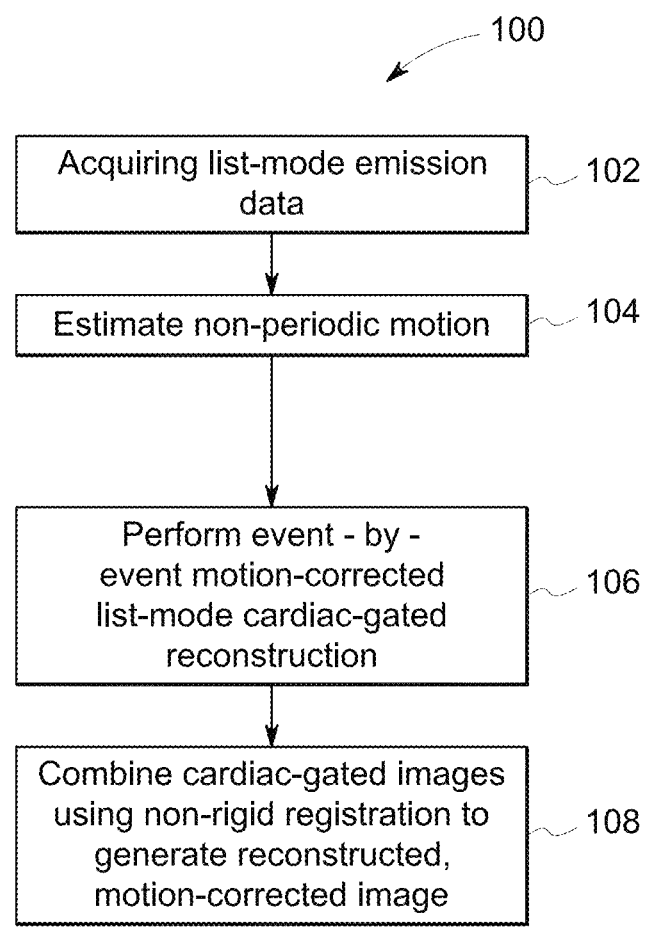
FIG. 4 is a flow chart of a method for motion compensation of medical imaging data, in accordance with aspects of the present disclosure.

FIG. 4 is a flow chart of a method 100 for motion compensation of medical imaging data. One or more steps of the method 100 may be performed by processing circuitry of the imaging systems discussed above or processing circuitry of a remote computing device having processing circuitry and memory circuitry. One or more of the steps of the method 100 may be performed simultaneously or in a different order from the order depicted in FIG. 4.

In certain embodiments, blocks 102-106 of the method 100 are continuously performed during a PET scan, while block 108 of the method 100 is performed subsequent to the PET scan. In certain embodiments, blocks 102-108 are performed subsequent to the PET scan. The method 100 includes acquiring list-mode emission data during a PET scan of heart of a subject (block 102). The method 100 also includes estimating non-periodic motion of a myocardium of the heart throughout (and during) the PET scan based on the list-mode emission data acquired during the PET scan of the heart of the subject (block 104). The non-periodic motions are due to respiratory and bulk body movements. In a preferred embodiment, the non-periodic motions are treated as rigid. In certain embodiments, a plurality (e.g., a four-dimensional (4D) stack) of consecutive (and short) frames (e.g., three-dimensional (3D) frames) may be generated from the list-mode emission data. The frames may be generated utilizing ultra-fast list-mode reconstruction as described in an article entitled "Ultra-Fast List-Mode Reconstruction of Short PET Frames and Example Applications" by Spanger-Bickell et al., J. Nucl. Med., Feb. 2021, Vol. 62, No. 2, pp. 287-292, Feb. 2021. In certain embodiments, each frame may span a second or less. In certain embodiments, each fame may span approximately 0.5 seconds. In certain embodiments, each frame may span approximately 0.1 seconds. In certain embodiments, each frame may span no more than a portion (e.g., 25 percent) of a mean respiratory cycle. In certain embodiments, prior to generating the frames, corrections (e.g., related to attenuation, random events, normalization, geometry of scanner, and other factors) may be prepared from the acquired list-mode emission data and utilized in the ultra-fast list-mode reconstruction.

In certain embodiments, estimating the non-periodic motion of the myocardium includes using rigid image registration with at least one degree of freedom on the consecutive frames with one of the frames utilized as a reference frame. For example, the non-periodic motion may be estimated over one or more translations along X-, Y-, and/or Z-coordinates. In certain embodiments, rotation may also be utilized in estimating motion. Any rotation utilized in estimating motion would be perpendicular to the long axis (i.e., rotation about a non-Cartesian axis). In certain embodiments, rigid image registration may include one, two, three, four, five, or six degrees of freedom (e.g., based on the number of translations and rotations). In certain embodiments, only translations may be utilized in estimating motion (e.g., one, two, or three translations). No respiratory gating is performed and no periodicity is assumed. During the estimation of the non-periodic motion of the myocardium using rigid image registration an actual position of the myocardium at every frame over an entirety of the PET scan. Also, the effects of bulk body movements are simultaneously estimated. In certain embodiments, the rigid registration is translation-only, image-based, rigid registration. In certain embodiments, the rigid image registration may be performed utilizing a least squares metric with a gradient descent optimizer after suitable image processing (e.g., cropping, smoothing, etc.). In certain embodiments, the rigid image registration may be performed utilizing mutual information or another technique. In certain embodiments, the reference frame for motion estimation may be chosen to ensure alignment of the list-mode emission data with an attenuation map with regards to a respiratory cycle.

Alternatively, in certain embodiments, respiratory gating may be utilized and the reconstruction of the frames may be tied to an ECG trigger from ECG signals acquired of the subject during the PET scan. In certain embodiments, estimating the non-periodic motion of the myocardium includes using non-rigid image registration on the consecutive frames. In certain embodiments, estimating the non-periodic motion of the myocardium includes using affine image registration on the consecutive frames. Affine registration allows for scaling and shearing of the myocardium, which may more accurately represent its non-periodic motion. In certain embodiments, estimating the non-periodic motion of the myocardium includes using non-rigid image registration on the consecutive frames. Such a registration strategy may more accurately estimate the true motion of the myocardium.

The method 100 further includes performing (on the full data set) event-by-event motion-corrected list-mode cardiac gated reconstruction on the list-mode emission data during the PET scan to generate cardiac-gated images (e.g., series of cardiac-gated images) with the non-periodic motion removed (block 106). The cardiac gated series presents the heart at a fixed position with only cardiac motion between gates. Once the non-periodic motion is estimated (e.g., block 104), the short frames are discarded. In certain embodiments, the event-by-event motion-corrected list-mode cardiac gated reconstruction includes performing motion correction on each event of the list-mode emission data and performing cardiac-gated reconstruction on the motion-corrected list-mode emission data. In certain embodiments, performing the motion correction includes repositioning or moving the endpoints of each list-mode event to account for the motion at the corresponding time point and calculating motion-aware corrections (e.g., related to a variety of factors such as sensitivity, normalization, attenuation, scatter, etc.) to be utilized in the motion correction. In certain embodiments, no motion-aware corrections may be applied to the data. The myocardial motion is assumed to be periodic. In certain embodiments, the performance of the cardiac-gated reconstruction is based on using triggers from ECG signals acquired of the subject. In certain embodiments, the performance of the cardiac-gated reconstruction is based on a data-driven gating approach.

The method 100 even further includes, subsequent to the PET scan, combining the cardiac-gated images using non-rigid image registration to generate a reconstructed, motion-corrected image or single volume (including all the data) of the heart (block 108). In particular, the cardiac-gated images are non-rigidly aligned and combined. In certain embodiments, the cardiac-gated images may be aligned using non-rigid image registration to a chosen gate. In certain embodiments, the cardiac-gated images may be aligned using non-rigid image registration to an aggregate gate. In certain embodiments, the reconstructed, motion-corrected image may be to a chosen gate (using all the counts). In certain embodiments, the reconstructed, motion-corrected image may be an aggregate of all the gates (using all the counts).

Figure 5:
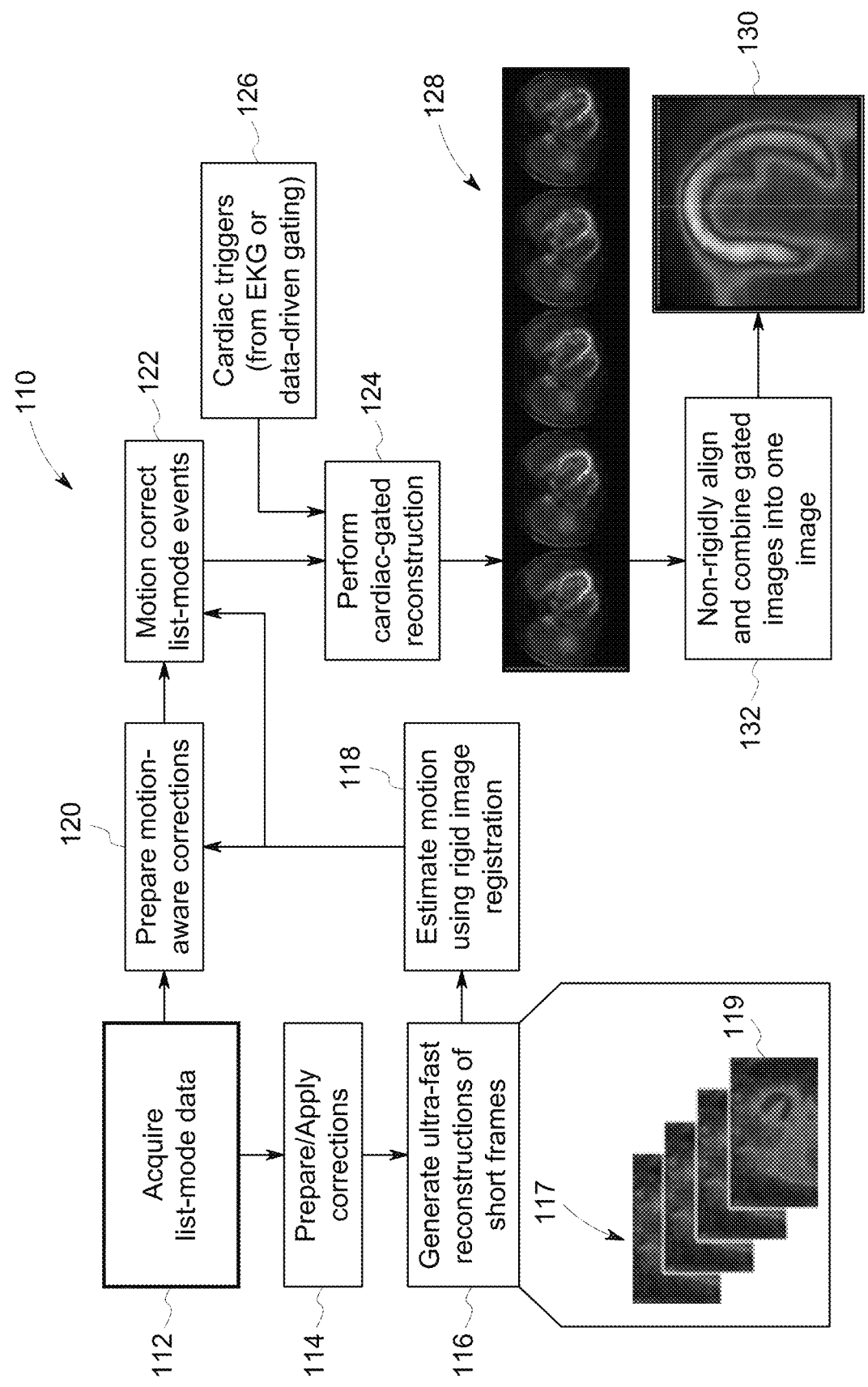
FIG. 5 is a schematic view of a method for motion compensation of medical imaging data (e.g., utilizing rigid image registration to estimate non-periodic motion), in accordance with aspects of the present disclosure.

FIG. 5 is a schematic view of a method 110 for motion compensation of medical imaging data (e.g., utilizing rigid image registration to estimate non-periodic motion). In certain embodiments, all of the steps of the method 110 are performed subsequent to the PET scan. In certain embodiments, all of the steps of the method 110 are performed during the PET scan with the exception of the last step (block 132) which is performed subsequent to the PET scan. One or more steps of the method 110 may be performed by processing circuitry of the imaging systems discussed above or processing circuitry of a remote computing device having processing circuitry and memory circuitry. One or more of the steps of the method 110 may be performed simultaneously or in a different order from the order depicted in FIG. 5.

The method 110 includes acquiring list-mode emission data during a PET scan of heart of a subject (block 112). The method 110 also includes preparing and applying corrections to the list-mode emission data (block 114). The corrections may be for a variety of factors such as attenuation, geometry of the scanner, random events, normalization, and so forth.

The method 110 further includes generating a plurality of short, consecutive frames from the acquired list-mode emission data (with the corrections applied) (block 116). As depicted in FIG. 5, the generation of the frames results in a 4D stack 117 of 3D frames 119. The frames may be generated utilizing ultra-fast list-mode reconstruction. In certain embodiments, each frame may span a second or less. In certain embodiments, each fame may span approximately 0.5 seconds. In certain embodiments, each frame may span approximately 0.1 seconds. In certain embodiments, each frame may span no more than a portion (e.g., 25 percent) of a mean respiratory cycle. In certain embodiments, the framing of the data into the short frames may be based on the cardiac phases to allow frames from corresponding phases in the cardiac cycle to be registered to each other. The cardiac cycle phase information can be derived from an electrocardiogram measurement or using a data-driven technique.

The method 110 still further includes estimating non-periodic motion of a myocardium of the heart throughout (and during) the PET scan based on the list-mode emission data acquired during the PET scan of the heart of the subject utilizing rigid image registration (block 118). The non-periodic motions are due to respiratory and bulk body movements. The non-periodic motions are treated as rigid. No respiratory gating is performed and no periodicity is assumed. The rigid image registration includes at least one degree of freedom when utilized on the consecutive frames with one of the frames utilized as a reference frame. For example, the non-periodic motion may be estimated over one or more translations along X-, Y-, and/or Z-coordinates. In certain embodiments, rotation may also be utilized in estimating motion. In certain embodiments, a single rotation may be utilized in estimating motion and would be parallel to the long axis of the heart (i.e., rotation about a non-Cartesian axis). In certain embodiments, rigid image registration may include one, two, three, four, five, or six degrees of freedom (e.g., based on the number of translations and rotations). In certain embodiments, only translations may be utilized in estimating motion (e.g., one, two, or three translations). The reference frame for motion estimation may be chosen to ensure alignment of the list-mode emission data with an attenuation map with regards to a respiratory cycle. During the estimation of the non-periodic motion of the myocardium using rigid image registration an actual position of the myocardium at every frame over an entirety of the PET scan. As a result, the effects of bulk body movements are simultaneously estimated. In certain embodiments, the rigid registration is translation-only, image-based, rigid registration. In certain embodiments, the rigid image registration may be performed utilizing a least squares metric with a gradient descent optimizer after suitable image processing (e.g., cropping, smoothing, etc.). In certain embodiments, a full-width at half-maximum (FWHM) Gaussian filter may be utilized for smoothing. In certain embodiments, the rigid image registration may be performed utilizing mutual information or another technique. In certain embodiments, an affine registration is utilized. In certain embodiments, a non-rigid registration is utilized.

Once the non-periodic motion is estimated (e.g., block 118), the short frames are discarded. The method 110 includes preparing or calculating motion-aware corrections to be utilized in motion correction (block 120). The motion-aware corrections may relate to variety of factors such as sensitivity, normalization, attenuation, scatter, and so forth. The method 110 also includes performing motion correction on each event of the list-mode events (all of the data) (block 122). Performing motion correction includes applying the motion-aware corrections to the list-mode events. In addition, performing motion correction includes repositioning or moving the endpoints of each list-mode event to account for the estimated motion.

Upon motion correcting the list-mode events, the method 110 includes performing cardiac-gated reconstruction on the motion-corrected list mode events (of the full data set) to generate cardiac-gated images with the non-periodic motion removed (block 124). Since myocardial motion is assumed to be periodic, cardiac triggers 126 are utilized for phase-based gating. In certain embodiments, the performance of the cardiac-gated reconstruction is based on using triggers 126 from ECG signals acquired of the subject. In certain embodiments, the performance of the cardiac-gated reconstruction is based on triggers 126 derived using a data-driven gating approach. The cardiac-gated reconstruction results in the generation of a cardiac-gated series of images 128.

The method 110 also includes non-rigidly aligning the images 128 using non-rigid image registration and combining the images 128 to form a fully motion corrected cardiac image 130 including all of the data (e.g., counts) (block 132). In certain embodiments, the cardiac-gated images 128 may be aligned using non-rigid image registration to a chosen gate. In certain embodiments, the cardiac-gated images 128 may be aligned using non-rigid image registration to an aggregate gate. In certain embodiments, the reconstructed, motion-corrected image 130 may be to a chosen gate (using all the counts). In certain embodiments, the reconstructed, motion-corrected image 130 may be an aggregate of all the gates (using all the counts).

Figure 6:
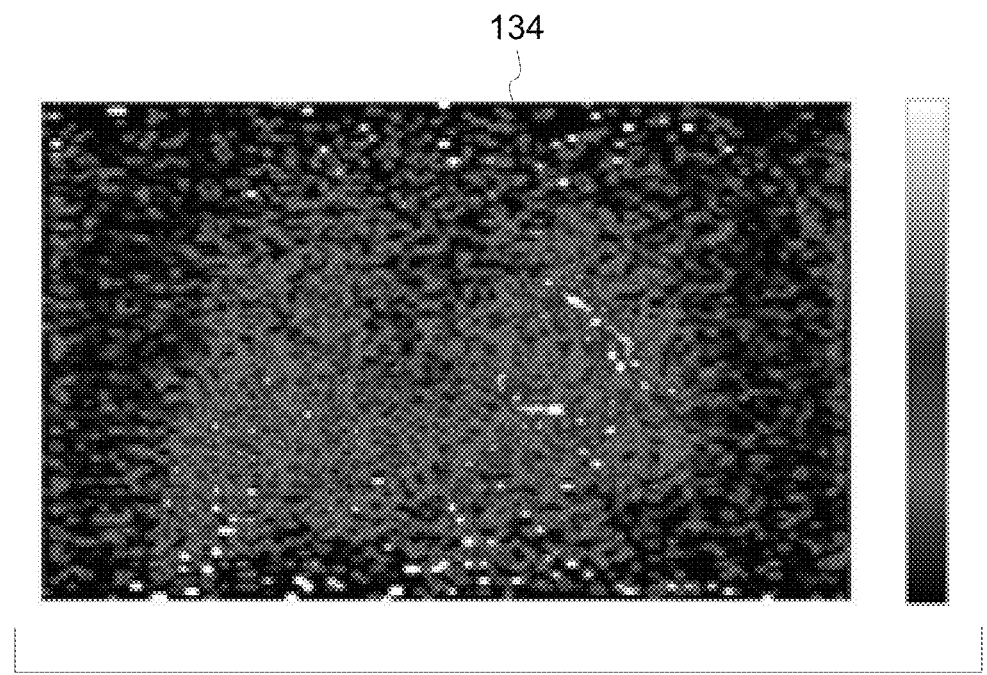
FIG. 6 is an example of an image from a frame utilized to estimate motion (e.g., non-periodic motion), in accordance with aspects of the present disclosure.
Figure 7:
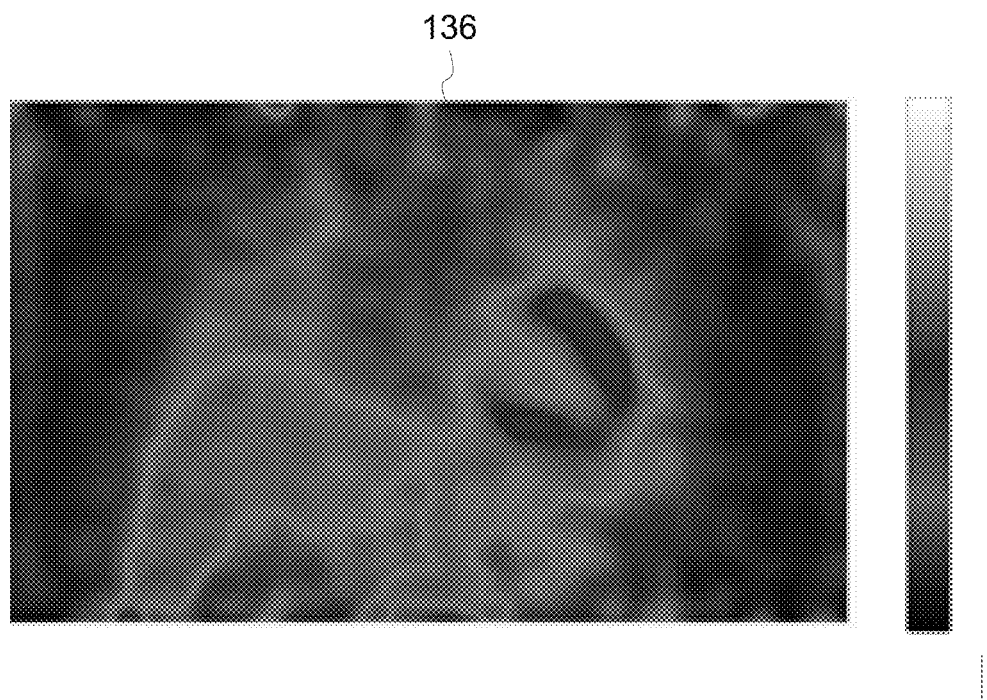
FIG. 7 is an example of the image in FIG. 6 (e.g., with smoothing), in accordance with aspects of the present disclosure.

FIG. 6 is an example of an image 134 from a frame utilized to estimate motion (e.g., non-periodic motion). The image 134 is of a coronal slice through the myocardium from a frame having a duration of 0.5 seconds. The frame was generated utilizing ultra-fast list-mode reconstruction as discussed above. The image 134 in FIG. 6 has had no smoothing applied. As noted above, in certain embodiments, each frame may span a second or less. In certain embodiments, each fame may span approximately 0.5 seconds as with the frame in FIG. 6. In certain embodiments, each frame may span approximately 0.1 seconds. In certain embodiments, each frame may span no more than a portion (e.g., 25 percent) of a mean respiratory cycle. FIG. 7 is an image 136 of the same frame with smoothing applied. The smoothing was applied utilizing a 12 millimeters (mm) FWHM Gaussian filter.

Figure 8:
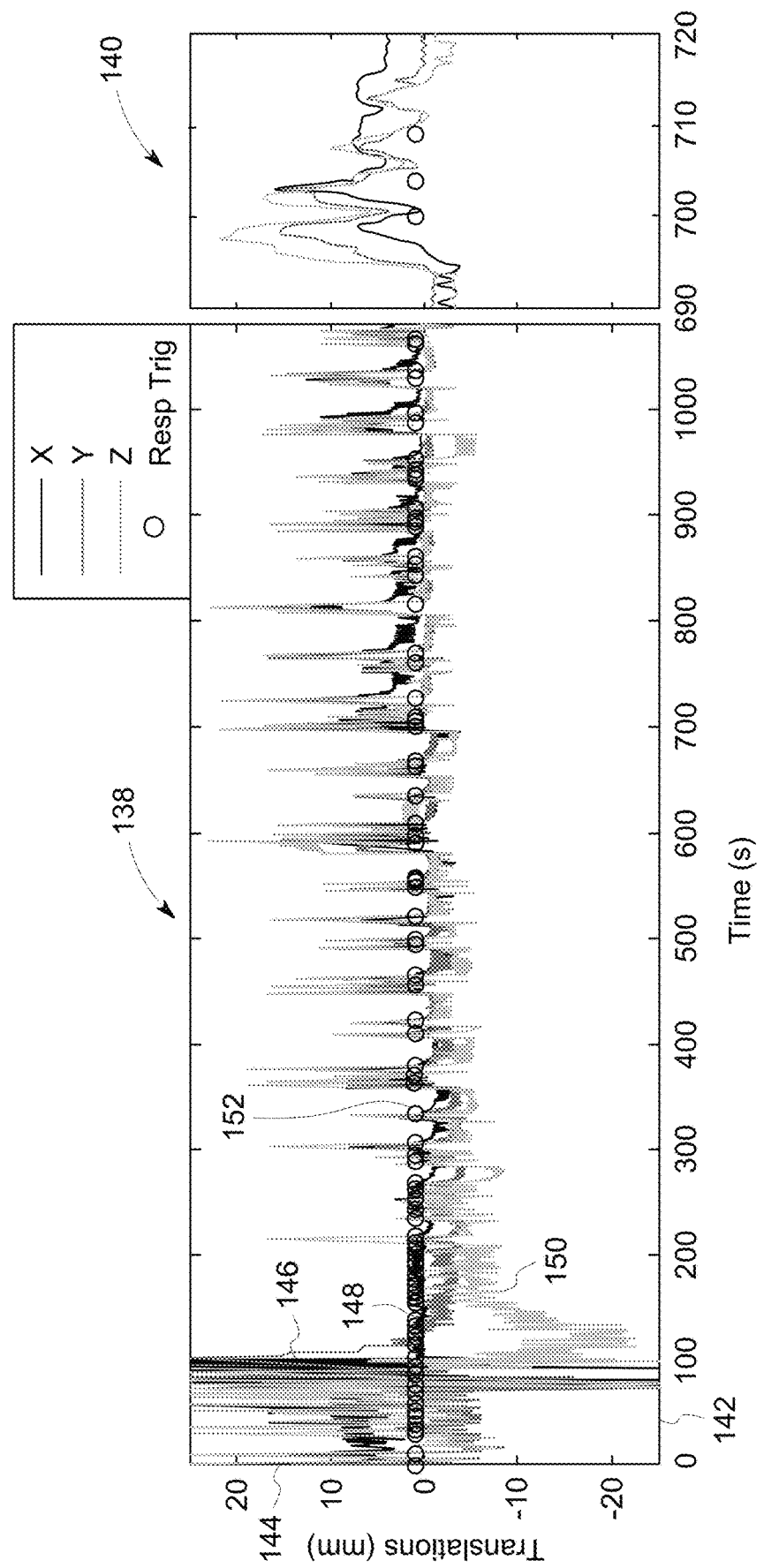
FIG. 8 is an example of a graph illustrating motion of myocardium, in accordance with aspects of the present disclosure.

FIG. 8 is an example of a graph 138 illustrating motion of myocardium. To the right of the graph 138 in FIG. 8 is a zoomed section 140 of the graph 138. The motion estimated in the graph 138 is rigid (translation only), non-periodic motion derived from applying rigid image registration to consecutive frames (e.g., generated utilizing ultra-fast list-mode reconstruction) generated from list-mode emission data from a PET scan. The motion is estimated over 3 translations only (e.g., along X-, Y-, and Z-coordinates). The graph 138 includes an X-axis 142 representing time (e.g., in seconds) during the PET scan. The graph 138 also includes a Y-axis 144 representing translations in distance (e.g., mm) during the PET scan. Plots 146, 148, and 150 represent movements or translations in the X-coordinate, Y-coordinate, and Z-coordinate, respectively. Circles 152 represent respiratory triggers measured by external hardware during the acquisition of the PET data. The circles 152 are superimposed on the plots 146, 148, 150. The circles are shown only to demonstrate that they are in agreement with the estimated motion. In certain embodiments, rotation may also be utilized in estimating motion. As depicted in FIG. 8, the motion estimate may be somewhat unreliable before a certain period (e.g., approximately 200 seconds in the present dataset) due to the initial uptake of bolus injection. In certain embodiments, only data after a certain period (i.e., after the initial uptake of the bolus injection) may be utilized in the subsequent motion correction and cardiac-gated reconstruction. The time period where the motion estimate may be somewhat unreliable may vary with different datasets. In certain embodiments, all of the data (e.g., from time 0 to the end of the PET scan) may be utilized in the subsequent motion correction and cardiac-gated reconstruction. In certain embodiments, various techniques may be utilized analyze the initial portion of data during the bolus uptake and gather meaningful data from during this period. Examples of such techniques would be to consider only specific volumes-of-interest around the myocardium to exclude the blood pool signal from the bolus injection, or to use principal component based methods to identify components corresponding to the blood pool from the bolus injection and exclude them.

Figure 9:
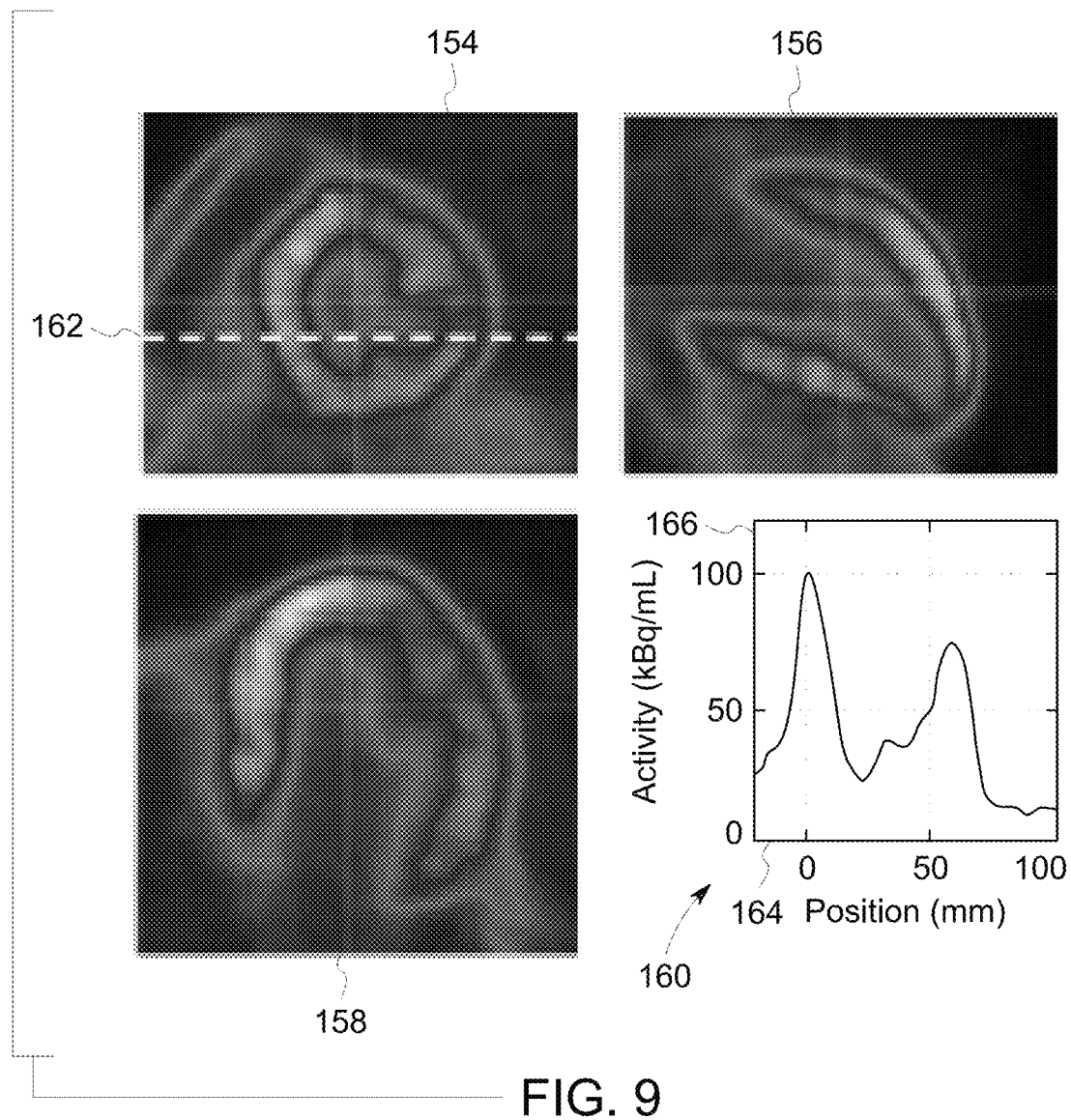
FIG. 9 are examples of images of myocardium reconstructed from PET data (e.g., without motion correction), in accordance with aspects of the present disclosure.
Figure 10:
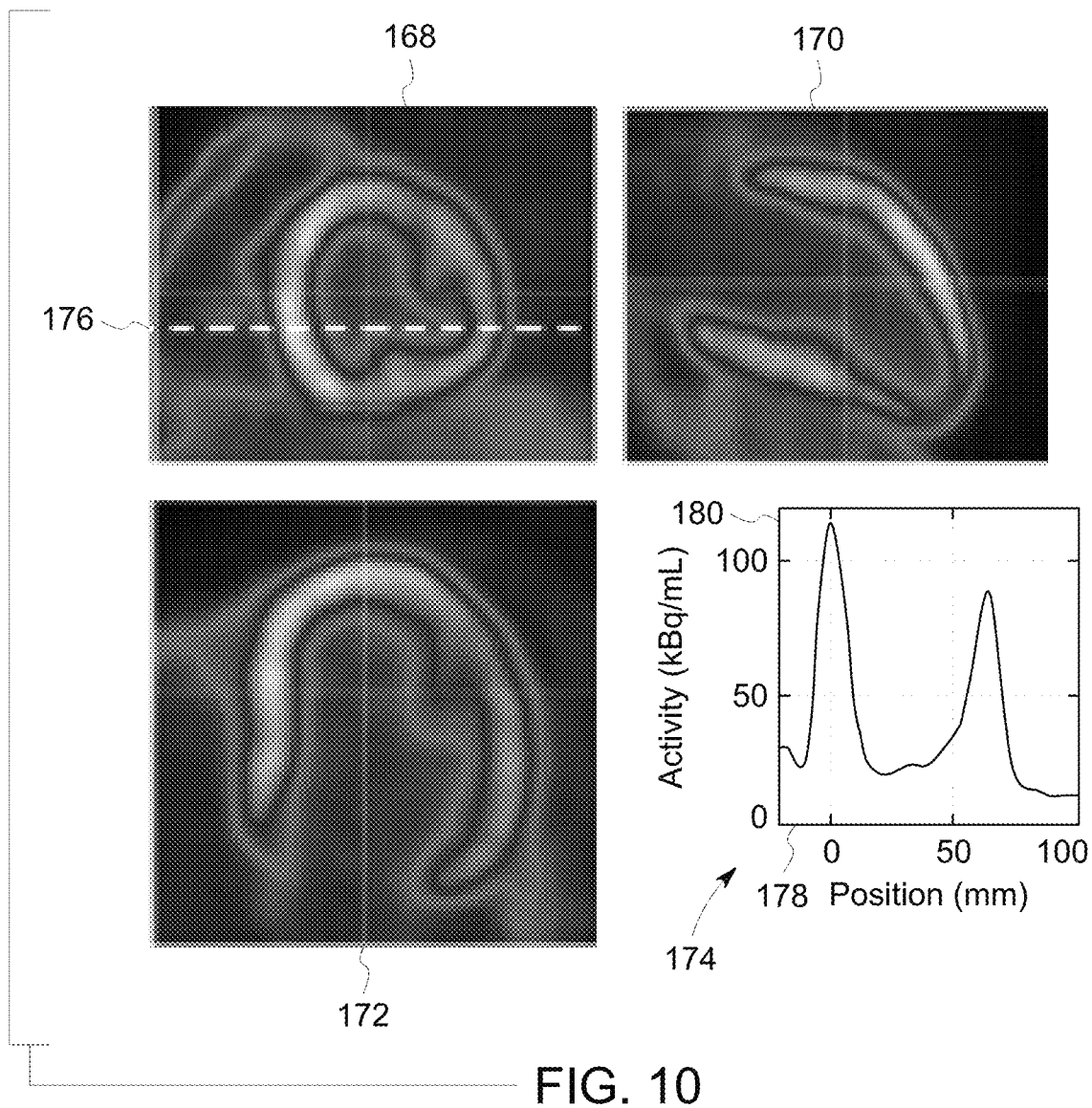
FIG. 10 are examples of images of myocardium reconstructed from PET data (e.g., with motion correction), in accordance with aspects of the present disclosure.

FIG. 9 are examples of images 154, 156, 158 of myocardium reconstructed from PET data. The images 154, 156, 158 are reconstructed without motion correction for non-periodic and periodic motion. In FIG. 9, graph 160 illustrates a profile of the myocardium in the image 154 at dashed line 162. The graph 160 includes an X-axis 164 representing position (e.g., in mm) and a Y-axis 166 representing radioactive activity in a region of interest (e.g., in kilobecquerel (kBq) per milliliter (mL)). FIG. 10 are examples of images 168, 170, 172 of myocardium reconstructed from PET data. The image 168, 170, 172 are reconstructed with motion correction for non-periodic and non-periodic motion. In particular, the images 168, 170, 172 are generated utilizing the techniques described above (e.g., the method 110 in FIG. 5). Each of the images 168, 170, 172 utilize all of the counts from the PET scan. In FIG. 10, graph 174 illustrates a profile of the myocardium in the image 168 at dashed line 176. The graph 174 includes an X-axis 178 representing position (e.g., in mm) and a Y-axis 180 representing radioactive activity in a region of interest (e.g., in kBq/mL). The images 168, 170, 172 in FIG. 10 exhibit good myocardial wall delineation, good signal-to-noise, and clearly reduced motion blurring.

Technical effects of the present disclosure include enabling the generation of motion-corrected cardiac images that are quantitatively more accurate than those without motion correction. In addition, the motion-corrected cardiac images have a superior signal-to-noise ratio compared to respiratory- or cardiac-gated images. These factors result in improved diagnostic quality of the images, more precise measurements of cardiac metrics, and new research opportunities. Further, the disclosed embodiments may lead to reduced scan time for a given signal-to-noise level.

This written description uses examples to disclose the present subject matter, including the best mode, and also to enable any person skilled in the art to practice the disclosed subject matter, including making and using any devices or systems and performing any incorporated methods. The patentable scope of the disclosed subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function]..." or "step for [perform]ing [a function]...", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. A computer-implemented method for motion compensation of medical imaging data, comprising:
  estimating, via a processor, non-periodic motion of a myocardium of a heart due to respiration and/or other body movements throughout a positron emission tomography (PET) scan based on list-mode emission data acquired during the PET scan of the heart of a subject; and
performing, via the processor, event-by-event motion-corrected list-mode reconstruction on the list-mode emission data to generate cardiac images with the non-periodic motion removed, wherein performing the event-by-event motion-corrected list-mode reconstruction on the list-mode emission data comprises performing cardiac-gated reconstruction on the list-mode emission data to generate cardiac-gated images with the non-periodic motion removed, wherein performing the event-by-event motion-corrected list mode cardiac-gated reconstruction comprises:
  performing, via the processor, motion correction on each event of the list-mode emission data; and
  performing, via the processor, cardiac-gated reconstruction on the motion-corrected list-mode emission data; and
  wherein performing motion correction on each event comprises:
    repositioning, via the processor, the endpoints of each event to account for motion at a corresponding time point; and
    calculating, via the processor, motion-aware corrections.

2. The computer-implemented method of claim 1, acquiring, via the processor, the list-mode emission data during the PET scan of the heart of the subject.

3. The computer-implemented method of claim 1, further comprising combining, via the processor, the cardiac-gated images using non-rigid image registration to generate a reconstructed, motion-corrected image of the heart.

4. The computer-implemented method of claim 1, wherein performing the cardiac-gated reconstruction is based on electrocardiogram signals acquired of the subject during the PET scan or a data-driven gating approach.

5. The computer-implemented method of claim 1, wherein performing the cardiac-gated reconstruction is based on both motion-corrected list-mode emission data and the motion-aware corrections.

6. The computer-implemented method of claim 3, wherein the reconstructed, motion-corrected image of the heart is for a specific gate.

7. The computer-implemented method of claim 3, wherein the reconstructed, motion-corrected image of the heart is an aggregate of all gates.

8. The computer-implemented method of claim 1, further comprising reconstructing the list-mode emission data into consecutive frames.

9. The computer-implemented method of claim 8, wherein each frame of the consecutive frames spans a second or less or spans no more than a portion of a mean respiratory cycle.

10. The computer-implemented method of claim 8, wherein estimating the non-periodic motion of the myocardium comprises using, via the processor, image registration with at least one degree of freedom on the consecutive frames with at least one of the consecutive frames utilized as a reference frame.

11. The computer-implemented method of claim 10, wherein estimating the non-periodic motion of the myocardium using image registration comprises estimating, via the processor, an actual position of the myocardium at every frame of the consecutive frames over an entirety of the PET scan.

12. The computer-implemented method of claim 10, wherein estimating the non-periodic motion of the myocardium using image registration comprises using rigid image registration on the consecutive frames.

13. The computer-implemented method of claim 10, wherein estimating the non-periodic motion of the myocardium using image registration comprises using non-rigid image registration on the consecutive frames.

14. The computer-implemented method of claim 10, wherein estimating the non-periodic motion of the myocardium using image registration comprises using affine image registration on the consecutive frames.

15. The computer-implemented method of claim 8, wherein reconstructing the list-mode emission data into consecutive frames is based on cardiac phase information.

16. A system for motion compensation of medical imaging data, comprising:
  a memory encoding processor-executable routines;
  a processing component configured to access the memory and to execute the processor-executable routines, wherein the routines, when executed by the processing component, cause the processing component to:
    estimate non-periodic motion of a myocardium of a heart due to respiration and/or other body movements throughout a positron emission tomography (PET) scan based on list-mode emission data acquired during the PET scan of the heart of a subject; and
  perform event-by-event motion-corrected list-mode reconstruction on the list-mode emission data to generate cardiac images with the non-periodic motion removed, wherein performing the event-by-event motion-corrected list-mode reconstruction on the list-mode emission data comprises performing cardiac-gated reconstruction on the list-mode emission data to generate cardiac-gated images with the non-periodic motion removed, wherein performing the event-by-event motion-corrected list mode cardiac-gated reconstruction comprises:
    performing, via the processor, motion correction on each event of the list-mode emission data; and
    performing, via the processor, cardiac-gated reconstruction on the motion-corrected list-mode emission data; and
  wherein performing motion correction on each event comprises:
    repositioning, via the processor, the endpoints of each event to account for motion at a corresponding time point; and
    calculating, via the processor, motion-aware corrections.

17. A non-transitory computer-readable medium, the computer-readable medium comprising processor-executable code that when executed by a processor, causes the processor to:

estimate non-periodic motion of a myocardium of a heart due to respiration and/or other body movements throughout a positron emission tomography (PET) scan based on list-mode emission data acquired during the PET scan of the heart of a subject; and perform event-by-event motion-corrected list-mode reconstruction on the list-mode emission data to generate cardiac images with the non-periodic motion removed, wherein performing the event-by-event motion-corrected list-mode reconstruction on the list-mode emission data comprises performing cardiac-gated reconstruction on the list-mode emission data to generate cardiac-gated images with the non-periodic motion removed, wherein performing the event-by-event motion-corrected list mode cardiac-gated reconstruction comprises:

performing, via the processor, motion correction on each event of the list-mode emission data; and performing, via the processor, cardiac-gated reconstruction on the motion-corrected list-mode emission data; and wherein performing motion correction on each event comprises:

repositioning, via the processor, the endpoints of each event to account for motion at a corresponding time point; and calculating, via the processor, motion-aware corrections.

* * * * *